US011883071B2

(12) United States Patent
Lindekugel

(10) Patent No.: US 11,883,071 B2
(45) Date of Patent: Jan. 30, 2024

(54) INTRAOSSEOUS ACCESS DEVICE

(71) Applicant: C. R. Bard, Inc., Franklin Lakes, NJ (US)

(72) Inventor: Eric W. Lindekugel, Salt Lake City, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 330 days.

(21) Appl. No.: 17/152,509

(22) Filed: Jan. 19, 2021

(65) Prior Publication Data
US 2021/0137558 A1 May 13, 2021

Related U.S. Application Data

(62) Division of application No. 15/796,471, filed on Oct. 27, 2017, now Pat. No. 10,893,887.
(Continued)

(51) Int. Cl.
*A61B 17/34* (2006.01)
*A61M 39/02* (2006.01)
(Continued)

(52) U.S. Cl.
CPC ...... *A61B 17/3472* (2013.01); *A61B 17/3415* (2013.01); *A61B 17/3423* (2013.01);
(Continued)

(58) Field of Classification Search
CPC ............ A61B 17/3472; A61B 17/3423; A61B 17/3415; A61B 17/3496; A61B 17/3494;
(Continued)

(56) References Cited

U.S. PATENT DOCUMENTS 2,773,501 A 12/1956 Young
3,071,135 A 1/1963 Baldwin et al.
(Continued)

FOREIGN PATENT DOCUMENTS

EP 0232600 A1 8/1987
EP 0548612 A1 6/1993
(Continued)

OTHER PUBLICATIONS

PCT/US2021/042040 filed Jul. 16, 2021 International Search Report and Written Opinion dated Oct. 4, 2021.
(Continued)

*Primary Examiner* — Theodore J Stigell
*Assistant Examiner* — Nidah Hussain
(74) *Attorney, Agent, or Firm* — Rutan & Tucker LLP

(57) ABSTRACT

An intraosseous access device can include a device body, a trocar needle, and an intraosseous catheter removably disposed on the trocar needle. The device body can be configured to enable a user of the access device to manually insert a distal tip of the trocar needle through a skin surface of a body of a patient to an external surface of a bone of the patient. The intraosseous access device can include a first advancement member configured to provide a first distal advancement force sufficient to distally advance a distal tip of the trocar needle and the catheter through a skin surface to an external surface of a bone of a patient, and a second advancement member configured to provide a second distal advancement force sufficient to distally advance the distal tip of the trocar needle and the catheter through the external surface of the bone.

14 Claims, 10 Drawing Sheets

Related U.S. Application Data

(60) Provisional application No. 62/413,879, filed on Oct. 27, 2016.

(51) Int. Cl.
 *A61M 5/158* (2006.01)
 *A61M 25/06* (2006.01)
 *A61M 39/10* (2006.01)

(52) U.S. Cl.
 CPC ...... *A61B 17/3494* (2013.01); *A61B 17/3496* (2013.01); *A61M 5/158* (2013.01); *A61M 25/065* (2013.01); *A61M 39/0247* (2013.01); *A61M 39/10* (2013.01); *A61M 2039/025* (2013.01); *A61M 2039/0273* (2013.01); *A61M 2039/0291* (2013.01)

(58) Field of Classification Search
 CPC ......... A61B 10/025; A61B 2010/0208; A61M 5/158; A61M 25/065; A61M 25/0662; A61M 25/06; A61M 39/10; A61M 39/0247; A61M 2039/0273; A61M 5/46; A61M 2210/02
 USPC ...................................................... 604/513
 See application file for complete search history.

(56) References Cited

U.S. PATENT DOCUMENTS

| | | |
|---|---|---|
| 3,166,189 A | 1/1965 | Disston |
| 3,329,261 A | 7/1967 | Serany, Jr. et al. |
| D222,312 S | 10/1971 | Kurtz et al. |
| 3,802,555 A | 4/1974 | Grasty et al. |
| 3,815,605 A | 6/1974 | Schmidt et al. |
| 3,991,765 A | 11/1976 | Cohen |
| 4,010,737 A | 3/1977 | Vilaghy et al. |
| 4,153,160 A | 5/1979 | Leigh |
| 4,226,328 A | 10/1980 | Beddow |
| 4,266,555 A | 5/1981 | Jamshidi |
| 4,314,565 A | 2/1982 | Lee |
| 4,383,530 A | 5/1983 | Bruno |
| 4,501,363 A | 2/1985 | Isbey, Jr. |
| 4,595,102 A | 6/1986 | Cianci et al. |
| 4,838,282 A | 6/1989 | Strasser et al. |
| 4,889,529 A | 12/1989 | Haindl |
| 4,925,448 A | 5/1990 | Bazaral |
| 4,952,207 A | 8/1990 | Lemieux |
| 4,964,854 A | 10/1990 | Luther |
| 4,969,870 A | 11/1990 | Kramer et al. |
| 5,040,542 A | 8/1991 | Gray |
| 5,042,558 A | 8/1991 | Hussey et al. |
| 5,053,017 A | 10/1991 | Chamuel |
| 5,098,391 A | 3/1992 | Pantages et al. |
| 5,122,114 A | 6/1992 | Miller et al. |
| 5,207,697 A | 5/1993 | Carusillo et al. |
| 5,263,939 A | 11/1993 | Wortrich |
| 5,290,267 A | 3/1994 | Zimmermann |
| 5,312,364 A | 5/1994 | Jacobs |
| 5,322,163 A | 6/1994 | Foos |
| 5,332,398 A | 7/1994 | Miller et al. |
| 5,364,367 A | 11/1994 | Banks et al. |
| 5,372,583 A | 12/1994 | Roberts et al. |
| 5,406,940 A | 4/1995 | Melzer et al. |
| 5,451,210 A | 9/1995 | Kramer et al. |
| 5,525,314 A | 6/1996 | Hurson |
| 5,554,154 A | 9/1996 | Rosenberg |
| 5,575,780 A | 11/1996 | Saito |
| 5,591,188 A | 1/1997 | Waisman |
| 5,601,559 A | 2/1997 | Melker et al. |
| 5,688,249 A | 11/1997 | Chang et al. |
| 5,746,720 A | 5/1998 | Stouder, Jr. |
| 5,772,678 A | 6/1998 | Thomason et al. |
| 5,779,708 A | 7/1998 | Wu |
| 5,807,275 A | 9/1998 | Jamshidi |
| 5,810,738 A | 9/1998 | Thomas, II |
| 5,810,826 A | 9/1998 | Åkerfeldt et al. |
| 5,817,052 A | 10/1998 | Johnson et al. |
| 5,853,393 A | 12/1998 | Bogert |
| 5,868,684 A | 2/1999 | Åkerfeldt et al. |
| 5,868,711 A | 2/1999 | Kramer et al. |
| 5,871,470 A | 2/1999 | McWha |
| 5,885,293 A | 3/1999 | McDevitt |
| 5,927,976 A | 7/1999 | Wu |
| 5,947,890 A | 9/1999 | Spencer et al. |
| 5,960,797 A | 10/1999 | Kramer et al. |
| 5,967,143 A | 10/1999 | Klappenberger |
| 5,990,382 A | 11/1999 | Fox |
| 6,012,586 A | 1/2000 | Misra |
| 6,068,121 A | 5/2000 | McGlinch |
| 6,117,108 A | 9/2000 | Woehr et al. |
| 6,135,769 A | 10/2000 | Kwan |
| 6,210,373 B1 | 4/2001 | Allmon |
| 6,210,376 B1 | 4/2001 | Grayson |
| 6,228,088 B1 | 5/2001 | Miller et al. |
| 6,247,928 B1 | 6/2001 | Meller et al. |
| 6,273,715 B1 | 8/2001 | Meller et al. |
| 6,419,490 B1 | 7/2002 | Kitchings Weathers, Jr. |
| 6,458,117 B1 | 10/2002 | Pollins, Sr. |
| 6,527,778 B2 | 3/2003 | Athanasiou et al. |
| 6,602,214 B2 | 8/2003 | Heinz et al. |
| 6,626,887 B1 | 9/2003 | Wu |
| 6,629,959 B2 | 10/2003 | Kuracina et al. |
| 6,641,395 B2 | 11/2003 | Kumar et al. |
| 6,652,490 B2 | 11/2003 | Howell |
| 6,692,471 B2 | 2/2004 | Boudreaux |
| 6,761,726 B1 | 7/2004 | Findlay et al. |
| 6,814,734 B2 | 11/2004 | Chappuis et al. |
| 6,830,562 B2 | 12/2004 | Mogensen et al. |
| 6,875,219 B2 | 4/2005 | Arramon et al. |
| 6,905,486 B2 | 6/2005 | Gibbs |
| 6,916,292 B2 | 7/2005 | Morawski et al. |
| 6,984,213 B2 | 1/2006 | Horner et al. |
| 6,991,096 B2 | 1/2006 | Gottlieb et al. |
| 6,997,907 B2 | 2/2006 | Safabash et al. |
| 7,112,191 B2 | 9/2006 | Daga |
| 7,135,031 B2 | 11/2006 | Flint |
| 7,179,244 B2 | 2/2007 | Smith et al. |
| 7,214,208 B2 | 5/2007 | Vaillancourt et al. |
| 7,278,987 B2 | 10/2007 | Solazzo |
| 7,347,838 B2 | 3/2008 | Kulli |
| 7,347,840 B2 | 3/2008 | Findlay et al. |
| 7,399,306 B2 | 7/2008 | Reiley et al. |
| 7,407,493 B2 | 8/2008 | Cane' |
| 7,410,053 B2 | 8/2008 | Bowen et al. |
| 7,434,687 B2 | 10/2008 | Itou et al. |
| 7,458,954 B2 | 12/2008 | Ferguson et al. |
| 7,513,888 B2 | 4/2009 | Sircom et al. |
| 7,530,965 B2 | 5/2009 | Villa et al. |
| 7,534,227 B2 | 5/2009 | Kulli |
| 7,569,033 B2 | 8/2009 | Greene et al. |
| 7,582,102 B2 | 9/2009 | Heinz et al. |
| 7,588,559 B2 | 9/2009 | Aravena et al. |
| 7,658,725 B2 | 2/2010 | Bialecki et al. |
| 7,670,328 B2 | 3/2010 | Miller |
| 7,699,807 B2 | 4/2010 | Faust et al. |
| 7,699,850 B2 | 4/2010 | Miller |
| 7,736,332 B2 | 6/2010 | Carlyon et al. |
| 7,743,918 B2 | 6/2010 | Itou et al. |
| 7,749,225 B2 | 7/2010 | Chappuis et al. |
| 7,798,994 B2 | 9/2010 | Brimhall |
| 7,811,260 B2 | 10/2010 | Miller et al. |
| 7,815,642 B2 | 10/2010 | Miller |
| 7,828,773 B2 | 11/2010 | Swisher et al. |
| 7,828,774 B2 | 11/2010 | Harding et al. |
| 7,833,204 B2 | 11/2010 | Picha |
| 7,842,038 B2 | 11/2010 | Haddock et al. |
| 7,850,620 B2 | 12/2010 | Miller et al. |
| 7,850,650 B2 | 12/2010 | Breitweiser |
| D633,199 S | 2/2011 | MacKay et al. |
| 7,899,528 B2 | 3/2011 | Miller et al. |
| 7,905,857 B2 | 3/2011 | Swisher |
| 7,951,089 B2 | 5/2011 | Miller |
| 7,955,297 B2 | 6/2011 | Radmer et al. |

(56) References Cited

U.S. PATENT DOCUMENTS

| | | |
|---|---|---|
| 7,972,339 B2 | 7/2011 | Nassiri et al. |
| 7,976,498 B2 | 7/2011 | Swisher et al. |
| 7,976,502 B2 | 7/2011 | Baid |
| 8,038,664 B2 | 10/2011 | Miller et al. |
| 8,043,253 B2 | 10/2011 | Kraft et al. |
| 8,043,265 B2 | 10/2011 | Abe et al. |
| 8,096,973 B2 | 1/2012 | Snow et al. |
| 8,142,365 B2 | 3/2012 | Miller |
| 8,152,771 B2 | 4/2012 | Mogensen et al. |
| 8,162,904 B2 | 4/2012 | Takano et al. |
| 8,167,899 B2 | 5/2012 | Justis et al. |
| 8,231,547 B2 | 7/2012 | Deck et al. |
| 8,235,945 B2 | 8/2012 | Baid |
| 8,240,468 B2 | 8/2012 | Wilkinson et al. |
| 8,246,584 B2 | 8/2012 | Aravena et al. |
| 8,273,053 B2 | 9/2012 | Saltzstein |
| 8,292,891 B2 | 10/2012 | Browne et al. |
| 8,308,693 B2 | 11/2012 | Miller et al. |
| 8,333,769 B2 | 12/2012 | Browne et al. |
| 8,356,598 B2 | 1/2013 | Rumsey |
| 8,357,163 B2 | 1/2013 | Sidebotham et al. |
| 8,388,623 B2 | 3/2013 | Browne et al. |
| 8,414,539 B1 | 4/2013 | Kuracina et al. |
| 8,419,683 B2 | 4/2013 | Miller et al. |
| 8,480,632 B2 | 7/2013 | Miller et al. |
| 8,480,672 B2 | 7/2013 | Browne et al. |
| 8,486,027 B2 | 7/2013 | Findlay et al. |
| 8,506,568 B2 | 8/2013 | Miller |
| 8,529,576 B2 | 9/2013 | Krueger et al. |
| 8,535,271 B2 | 9/2013 | Fuchs et al. |
| 8,562,615 B2 | 10/2013 | Browne et al. |
| 8,584,849 B2 | 11/2013 | McCaffrey |
| 8,641,715 B2 | 2/2014 | Miller |
| 8,647,257 B2 | 2/2014 | Jansen et al. |
| 8,656,929 B2 | 2/2014 | Miller et al. |
| 8,657,790 B2 | 2/2014 | Tal et al. |
| 8,662,306 B2 | 3/2014 | Agrawal |
| 8,663,231 B2 | 3/2014 | Browne et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,758,383 B2 | 6/2014 | Geist |
| 8,771,230 B2 | 7/2014 | White et al. |
| 8,801,663 B2 | 8/2014 | Woehr |
| 8,812,101 B2 | 8/2014 | Miller et al. |
| 8,814,835 B2 | 8/2014 | Baid |
| 8,828,001 B2 | 9/2014 | Stearns et al. |
| 8,870,872 B2 | 10/2014 | Miller |
| 8,893,883 B2 | 11/2014 | Valaie et al. |
| D720,471 S | 12/2014 | Angel et al. |
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,131,925 B2 | 9/2015 | Kraft et al. |
| 9,149,625 B2 | 10/2015 | Woehr et al. |
| 9,173,679 B2 | 11/2015 | Tzachar et al. |
| 9,186,217 B2 | 11/2015 | Goyal |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,451,968 B2 | 9/2016 | Miller et al. |
| 9,451,983 B2 | 9/2016 | Windolf |
| 9,480,483 B2 | 11/2016 | Browne et al. |
| 9,486,604 B2 | 11/2016 | Murray et al. |
| 9,504,477 B2 | 11/2016 | Miller et al. |
| 9,545,243 B2 | 1/2017 | Miller et al. |
| 9,615,816 B2 | 4/2017 | Woodard |
| 9,615,838 B2 | 4/2017 | Nino et al. |
| 9,623,210 B2 | 4/2017 | Woehr |
| 9,636,484 B2 | 5/2017 | Baid |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,744,333 B2 | 8/2017 | Terzibashian |
| 9,782,546 B2 | 10/2017 | Woehr |
| 9,788,843 B2 | 10/2017 | Teisen et al. |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 9,999,444 B2 | 6/2018 | Geist et al. |
| 10,022,464 B2 | 7/2018 | Sarphati et al. |
| 10,039,897 B2 | 8/2018 | Norris et al. |
| 10,052,111 B2 | 8/2018 | Miller et al. |
| 10,064,694 B2 | 9/2018 | Connolly |
| 10,070,933 B2 | 9/2018 | Adler et al. |
| 10,070,934 B2 | 9/2018 | Kerns et al. |
| 10,080,864 B2 | 9/2018 | Terzibashian |
| 10,092,320 B2 | 10/2018 | Morgan et al. |
| 10,106,295 B2 | 10/2018 | Lockwood |
| 10,130,343 B2 | 11/2018 | Miller et al. |
| 10,136,878 B2 | 11/2018 | Tzachar et al. |
| 10,182,878 B2 | 1/2019 | Goyal |
| 10,238,420 B2 | 3/2019 | Karve et al. |
| 10,245,010 B2 | 4/2019 | Miller et al. |
| 10,251,812 B2 | 4/2019 | Tomes et al. |
| 10,258,783 B2 | 4/2019 | Miller et al. |
| 10,314,629 B2 | 6/2019 | Park et al. |
| 10,405,938 B2 | 9/2019 | Ramsey |
| 10,441,454 B2 | 10/2019 | Tanghoej et al. |
| 10,456,149 B2 | 10/2019 | Miller |
| 10,456,497 B2 | 10/2019 | Howell et al. |
| 10,595,896 B2 | 3/2020 | Miller |
| 10,722,247 B2 | 7/2020 | Browne et al. |
| 10,893,887 B2 | 1/2021 | Blanchard |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0162559 A1 | 8/2004 | Arramon et al. |
| 2004/0220497 A1 | 11/2004 | Findlay et al. |
| 2004/0243135 A1 | 12/2004 | Koseki |
| 2005/0033235 A1 | 2/2005 | Flint |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0148940 A1 | 7/2005 | Miller |
| 2005/0165403 A1* | 7/2005 | Miller .................. A61B 10/025 600/567 |
| 2005/0261693 A1* | 11/2005 | Miller ................ A61B 17/3476 606/80 |
| 2006/0015066 A1 | 1/2006 | Turieo et al. |
| 2006/0025723 A1 | 2/2006 | Ballarini |
| 2007/0016138 A1 | 1/2007 | Swisher et al. |
| 2007/0049945 A1 | 3/2007 | Miller |
| 2007/0191772 A1 | 8/2007 | Wojcik |
| 2007/0270775 A1 | 11/2007 | Miller et al. |
| 2008/0086142 A1 | 4/2008 | Kohm et al. |
| 2008/0119759 A1 | 5/2008 | McLain |
| 2008/0119821 A1 | 5/2008 | Agnihotri et al. |
| 2008/0140014 A1 | 6/2008 | Miller et al. |
| 2008/0154304 A1 | 6/2008 | Crawford et al. |
| 2008/0208136 A1 | 8/2008 | Findlay et al. |
| 2008/0215056 A1 | 9/2008 | Miller et al. |

(56) References Cited

U.S. PATENT DOCUMENTS

| | | |
|---|---|---|
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0105775 A1 | 4/2009 | Mitchell et al. |
| 2009/0118639 A1 | 5/2009 | Moos et al. |
| 2009/0204024 A1 | 8/2009 | Miller |
| 2009/0228014 A1 | 9/2009 | Stearns et al. |
| 2009/0306697 A1 | 12/2009 | Fischvogt |
| 2010/0030105 A1 | 2/2010 | Noishiki et al. |
| 2010/0082033 A1 | 4/2010 | Germain |
| 2010/0152616 A1 | 6/2010 | Beyhan et al. |
| 2010/0204649 A1 | 8/2010 | Miller et al. |
| 2010/0280410 A1 | 11/2010 | Moos et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2011/0137253 A1 | 6/2011 | Simonton et al. |
| 2012/0041454 A1 | 2/2012 | Johnstone |
| 2012/0202180 A1 | 8/2012 | Stock et al. |
| 2012/0203154 A1 | 8/2012 | Tzachar |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0079720 A1 | 3/2013 | Finnestad et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2013/0331840 A1 | 12/2013 | Teisen et al. |
| 2014/0039400 A1 | 2/2014 | Browne et al. |
| 2014/0046327 A1 | 2/2014 | Tzachar et al. |
| 2014/0074102 A1 | 3/2014 | Mandeen et al. |
| 2014/0081281 A1 | 3/2014 | Felder |
| 2014/0142577 A1 | 5/2014 | Miller |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276366 A1* | 9/2014 | Bourne ............ A61M 37/0015 604/22 |
| 2014/0276471 A1 | 9/2014 | Emery et al. |
| 2014/0276833 A1 | 9/2014 | Larsen et al. |
| 2014/0276839 A1 | 9/2014 | Forman et al. |
| 2014/0343454 A1 | 11/2014 | Miller et al. |
| 2014/0343497 A1 | 11/2014 | Baid |
| 2015/0011941 A1 | 1/2015 | Saeki |
| 2015/0126931 A1 | 5/2015 | Holm et al. |
| 2015/0127006 A1 | 5/2015 | Miller |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0058432 A1 | 3/2016 | Miller |
| 2016/0066954 A1 | 3/2016 | Miller et al. |
| 2016/0106441 A1 | 4/2016 | Teisen et al. |
| 2016/0136410 A1 | 5/2016 | Aklog et al. |
| 2016/0183974 A1 | 6/2016 | Miller |
| 2016/0228676 A1 | 8/2016 | Glithero et al. |
| 2016/0235949 A1 | 8/2016 | Baid |
| 2016/0354539 A1 | 12/2016 | Tan et al. |
| 2016/0361519 A1 | 12/2016 | Teoh et al. |
| 2017/0021138 A1 | 1/2017 | Sokolski |
| 2017/0043135 A1 | 2/2017 | Knutsson |
| 2017/0056122 A1 | 3/2017 | Ramsey |
| 2017/0105763 A1 | 4/2017 | Karve et al. |
| 2017/0136217 A1 | 5/2017 | Riesenberger et al. |
| 2017/0143395 A1 | 5/2017 | Park et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0303962 A1 | 10/2017 | Browne et al. |
| 2017/0303963 A1 | 10/2017 | Kilcoin et al. |
| 2018/0092662 A1 | 4/2018 | Rioux et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0154112 A1 | 6/2018 | Chan et al. |
| 2018/0206933 A1 | 7/2018 | Healey et al. |
| 2018/0221564 A1 | 8/2018 | Patel et al. |
| 2018/0236182 A1 | 8/2018 | Charlebois et al. |
| 2019/0021807 A1 | 1/2019 | Barnell et al. |
| 2019/0060607 A1 | 2/2019 | Yabu et al. |
| 2019/0076132 A1 | 3/2019 | Tzachar et al. |
| 2019/0125404 A1 | 5/2019 | Shippert |
| 2019/0150953 A1 | 5/2019 | Budyansky et al. |
| 2019/0151606 A1 | 5/2019 | Mottola et al. |
| 2019/0201053 A1 | 7/2019 | Ben Mocha et al. |
| 2019/0282244 A1 | 9/2019 | Muse |
| 2019/0328370 A1 | 10/2019 | Muse |
| 2019/0343556 A1 | 11/2019 | Coppedge et al. |
| 2021/0093358 A1 | 4/2021 | Lindekugel et al. |

FOREIGN PATENT DOCUMENTS

| | | |
|---|---|---|
| WO | 1997024151 A1 | 7/1997 |
| WO | 1998052638 A3 | 2/1999 |
| WO | 2004000408 A1 | 12/2003 |
| WO | 2005/046769 A2 | 5/2005 |
| WO | 05041790 A2 | 5/2005 |
| WO | 2005053506 A2 | 6/2005 |
| WO | 2005072625 A2 | 8/2005 |
| WO | 2006/047737 A2 | 5/2006 |
| WO | 2007018809 A2 | 2/2007 |
| WO | 2008002961 A2 | 1/2008 |
| WO | 2008016757 A2 | 2/2008 |
| WO | 2008033871 A2 | 3/2008 |
| WO | 2008033872 A2 | 3/2008 |
| WO | 2008033873 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011097311 A2 | 8/2011 |
| WO | 2011139294 A1 | 11/2011 |
| WO | 2013009901 A2 | 1/2013 |
| WO | 2013173360 A1 | 11/2013 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015/177612 A1 | 11/2015 |
| WO | 2016033016 A1 | 3/2016 |
| WO | 16053834 A1 | 4/2016 |
| WO | 2016163939 A1 | 10/2016 |
| WO | 18006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018/165334 A1 | 9/2018 |
| WO | 2018165339 A1 | 9/2018 |
| WO | 2019/051343 A1 | 3/2019 |
| WO | 2019051412 A1 | 3/2019 |

(56) References Cited

FOREIGN PATENT DOCUMENTS

| WO | 2019/215705 A1 | 11/2019 |
| WO | 2020/012051 A1 | 1/2020 |
| WO | 2021/062215 A1 | 4/2021 |

OTHER PUBLICATIONS

EP 17861304.8 filed Apr. 16, 2019 Extended European Search Report filed Jul. 28, 2020.
EP 17864208.8 filed May 24, 2019 Extended European Search Report filed May 19, 2020.
PCT/US 17/57270 filed Oct. 18, 2017 International Search Report and Written Opinion dated Jan. 12, 2018.
PCT/US2017/058863 filed Oct. 27, 2017 International Search Report and Written Opinion dated Jan. 29, 2018.
PCT/US2018/021398 filed Mar. 7, 2018 International search report and written opinion dated May 21, 2018.
PCT/US2020/052809 filed Sep. 25, 2020 International Search Report and Written Opinion dated Jan. 5, 2021.
U.S. Appl. No. 15/796,471, filed Oct. 27, 2017 Advisory Action dated Jun. 15, 2020.
U.S. Appl. No. 15/796,471, filed Oct. 27, 2017 Final Office Action dated Apr. 23, 2020.
U.S. Appl. No. 15/796,471, filed Oct. 27, 2017 Non-Final Office Action dated Oct. 30, 2019.
U.S. Appl. No. 15/796,471, filed Oct. 27, 2017 Notice of Allowance dated Jun. 15, 2020.
U.S. Appl. No. 15/796,471, filed Oct. 27, 2017 Restriction Requirement dated Jul. 8, 2019.
U.S. Appl. No. 17/183,820, filed Feb. 24, 2021 Non Final Office Action dated May 30, 2023.
U.S. Appl. No. 17/033,093, filed Sep. 25, 2020 Non-Final Office Action dated Mar. 2, 2023.
U.S. Appl. No. 17/033,093, filed Sep. 25, 2020 Restriction Requirement dated Nov. 15, 2022.
U.S. Appl. No. 17/183,820, filed Feb. 24, 2021 Restriction Requirement dated Feb. 13, 2023.
EP 20868558.6 filed Apr. 21, 2022 Extended European Search Report dated Aug. 11, 2023.
U.S. Appl. No. 17/033,093 filed Sep. 25, 2020 Advisory Action dated Oct. 4, 2023.
U.S. Appl. No. 17/033,093 filed Sep. 25, 2020 Final Office Action dated Sep. 8, 2023.
U.S. Appl. No. 17/183,820 filed Feb. 24, 2021 Final Office Action dated Sep. 28, 2023.

* cited by examiner

# INTRAOSSEOUS ACCESS DEVICE

CROSS-REFERENCE TO RELATED APPLICATIONS

This application is a division of U.S. patent application Ser. No. 15/796,471, filed Oct. 27, 2017, now U.S. Pat. No. 10,893,887, which claims the benefit of U.S. Provisional Patent Application No. 62/413,879, filed Oct. 27, 2016, each of which is incorporated herein by reference in its entirety.

BRIEF SUMMARY

Briefly summarized, present embodiments are directed to an access device configured for inserting an intraosseous catheter into an interior portion of a bone. Such access is desired in certain situations to enable rapid infusion of medicaments into the interior intraosseous portion of the bone, which medicaments can then be quickly assimilated into the body. In accordance with embodiments to be described, the access devices disclosed herein are capable of inserting the intraosseous catheter a predetermined distance into the bone interior, which enables the user of the device to accurately place the distal tip of the catheter where desired within the intraosseous region, in contrast to known intraosseous devices.

In one embodiment, an intraosseous access device is disclosed, comprising a device body, a trocar needle included with the device body, and an intraosseous catheter removably disposed on the trocar needle. The device body is configured to enable a user of the access device to manually insert a distal tip of the trocar needle through a skin surface of a body of a patient to an external surface of a bone of the patient. An advancement mechanism is also disclosed and is configured to selectively and distally advance the trocar needle and intraosseous catheter into an internal portion of the bone of the patient after the distal tip of the trocar needle has been inserted to the external surface of the bone.

In addition to the above, other access device and intraosseous catheter configurations are disclosed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present disclosure, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present disclosure are generally directed to an access device configured for inserting an intraosseous catheter into an interior portion of a bone. Such access is desired in certain situations to enable rapid infusion of medicaments into the interior intraosseous portion of the bone, which medicaments can then be quickly assimilated into the body. In accordance with embodiments to be described, the access devices disclosed herein are capable of inserting the intraosseous catheter a predetermined distance into the bone interior, which enables the user of the device to accurately place the distal tip of the catheter where desired within the intraosseous region, in contrast to known intraosseous devices.

Figure 1:
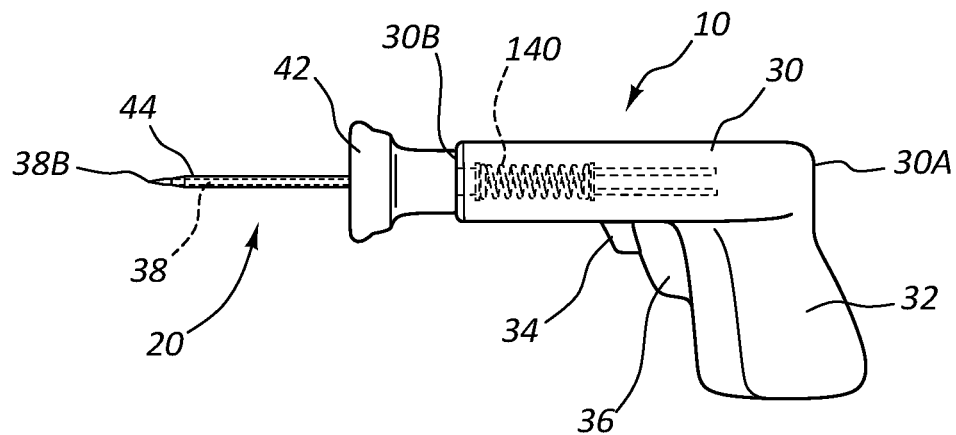
FIG. 1 is a side view of an intraosseous access device according to one embodiment.

FIG. 1 depicts various details of an intraosseous access device ("access device"), generally designated at 10, according to one embodiment. The access device 10 is shown with an intraosseous catheter ("catheter") 20, also referred to as an intraosseous cannula, removably included therewith. Though further details will be given below, in the present embodiment the catheter 20 generally includes a hub 42 and an attached cannula 44 that extends between a proximal end 44A and a distal end 44B. The cannula 44 is slidably received over a trocar needle ("trocar") 38 that distally extends from the access device 10 and terminates at a distal tip 38B.

As shown, the access device 10 includes a body 30 extending between a proximal end 30A and a distal end 30B. In the present embodiment, the body 30 is shaped to define a pistol grip 32 suitable for grasping by a user of the access device 10, though many other suitable shapes for the body are possible.

The body 30 houses an advancement mechanism configured to selectively advance the trocar 38 and catheter 20 included therewith in a distal direction during use of the access device 10. In the present embodiment, the advancement mechanism includes an internal spring that is mounted within the body 30 and operably connected to the trocar 38. The spring is selectively releasable by an actuator, such as a release trigger 36, as to advance the trocar 38 distally with respect to the body 30. This enables the trocar 38 and the catheter 20 included therewith to be driven into a bone of the patient, as will be described further below. As illustrated in FIG. 1, a safety switch 34 is also included and configured to prevent inadvertent actuation of the release trigger 36 by the user. In the present embodiment, the safety switch 34 is positioned adjacent the release trigger 36 and must be displaced from its original position, such as by sliding, so as to enable the release trigger to be actuated by a finger of the user, for instance. Of course, other safety switch and release trigger configurations can be employed.

Figure 2A:
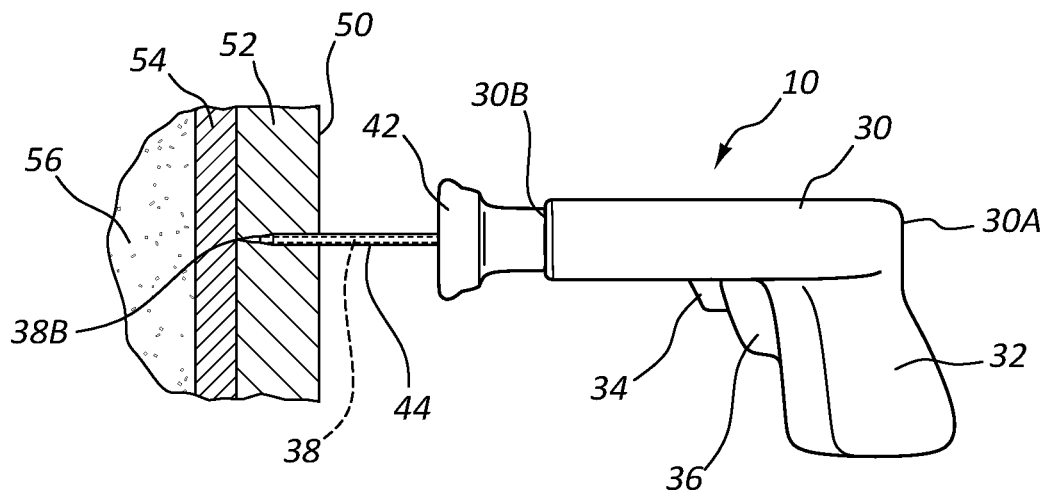
FIGS. 2A-2D depict various stages of use of an access device such as that shown in FIG. 1.
Figure 2B:
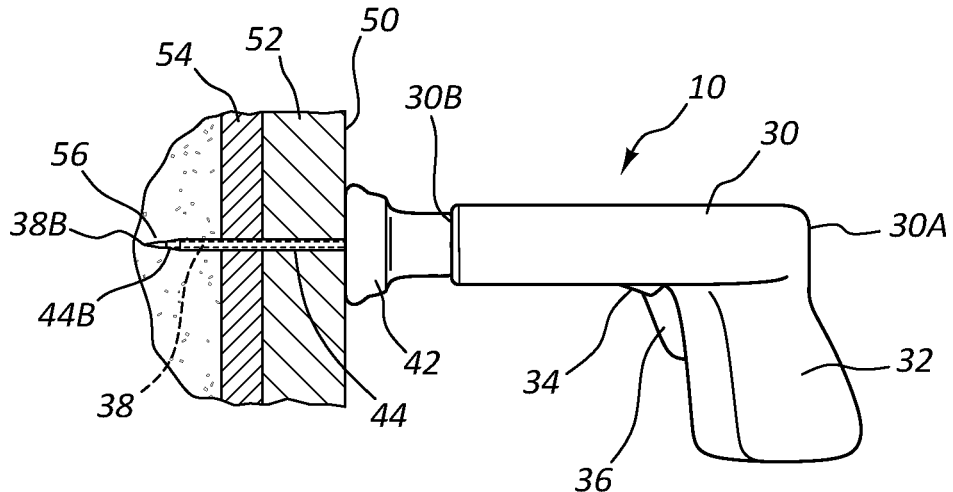

FIGS. 2A-2D depict various stages of use of the access device 10 in inserting the catheter 20 into a bone of a patient, according to one embodiment. For clarity, the hand of the user is omitted from the figures. As shown in FIG. 2A, the user grasps the body 30 of the access device and directs the distal tip 38B of the trocar 38 via manual force through a skin surface 50 and subcutaneous tissue 52 of the patient until the distal tip of the trocar impacts a wall ("bone wall") 54 of the bone. At this point, the safety switch 34 is disengaged by the user and the release trigger 36 is depressed by a finger of the user, which in turn causes the internal spring (or other suitable advancement mechanism) to distally drive the trocar distal tip 38B through the bone wall 54 and into the interior, bone marrow 56, of the bone, as seen in FIG. 2B. This also places the distal tip 44B of the catheter cannula 44 in the bone marrow 56, as desired. Note that the internal spring, as an advancement mechanism, serves as one example of a selective means for advancing the trocar and the catheter. It is appreciated that other structures and components can be employed to provide the same functionality, in other embodiments, including a drill, a chemical or other charges, controlled explosive charges, etc.

Note that the access device 10 and the advancement mechanism are configured to advance the cannula distal tip 44B a predetermined distance into the bone. In one embodiment, the predetermined distance can vary from about 0.25 inch to about 1 inch into the bone, though a variety of other possible depths are possible. The variation in predetermined depth may be needed in accessing bones of differing thicknesses. In one embodiment, a depth selector, such as a depth dial, can be included on the access device body 30. With such a depth dial, the user can select the desired depth that the advancement mechanism will advance the distal tip 44B of the cannula 44. The depth dial in such an embodiment can vary the pre-actuation compression of the spring so as to achieve a corresponding advancement of the trocar 38 and catheter 20 according to the depth dial setting. In other embodiments, other controls can be employed to vary actuation of the spring or other advancement mechanism according to predetermined desired depths. In yet another embodiment, the access device 10 can be configured to insert the trocar 38 and catheter 20 to one, pre-set depth.

Figure 2C:
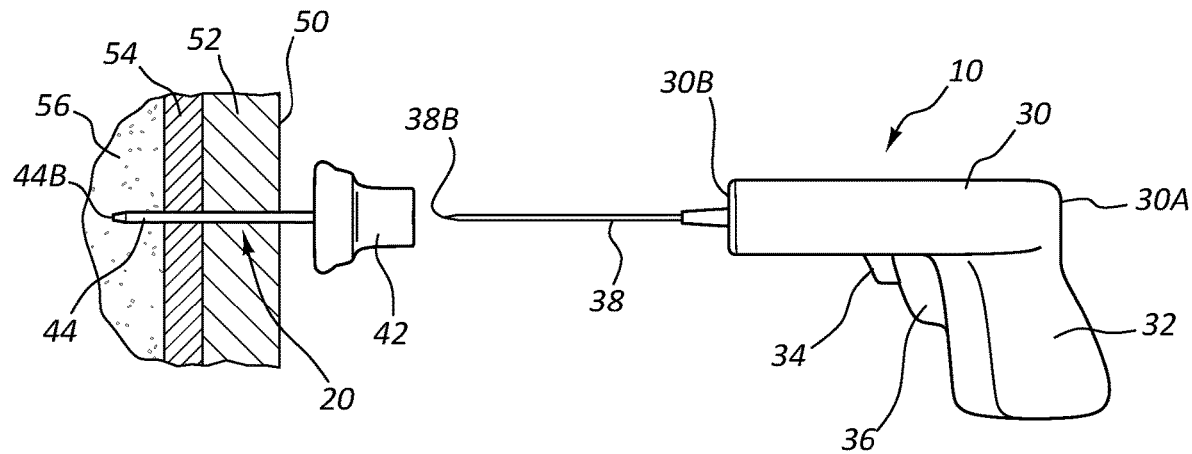
Figure 2D:
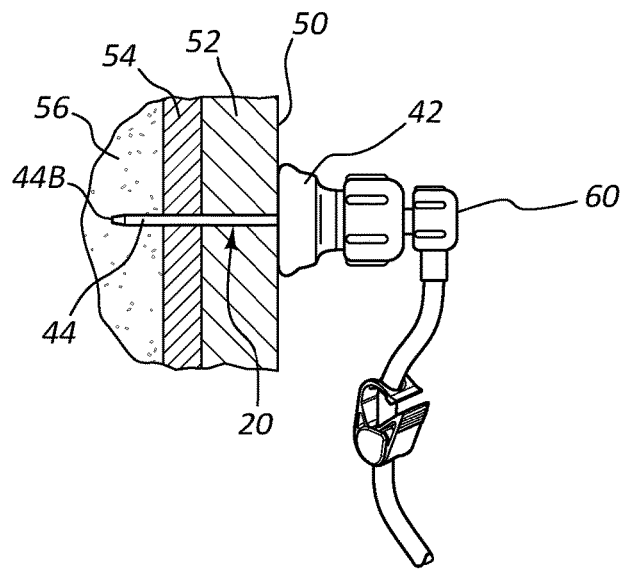

In FIG. 2C, the trocar 38 is withdrawn from the cannula 44 of the catheter 20 by proximally withdrawing the access device body 30, thus causing separation of the access device 10 from the catheter 20. After withdrawal of the access device 10, the cannula 44 remains in place with its distal tip 44B disposed within the bone marrow 56, as shown. Note that the catheter hub 42 is spaced apart from the skin surface 50 at this point. In FIG. 2D, the catheter 20 is adjusted such that the hub 42 is adjacent the skin surface 50, as explained in further detail below. Also, an extension set 60 is shown operably attached to the hub 42 so as to enable medicaments or other fluids to be infused through the catheter 20 and into the bone marrow 56 via the catheter cannula 44.

Figure 3A:
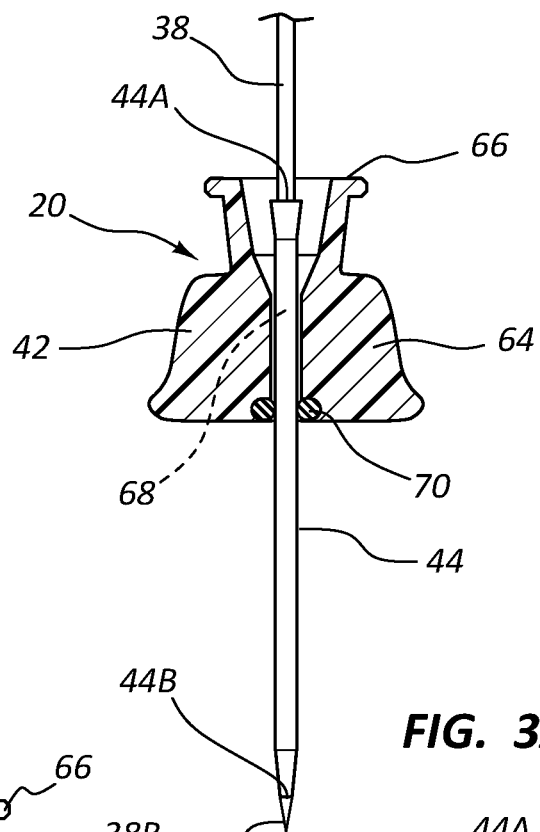
FIGS. 3A-3D depict various views of an intraosseous catheter according to one embodiment.
Figure 3B:
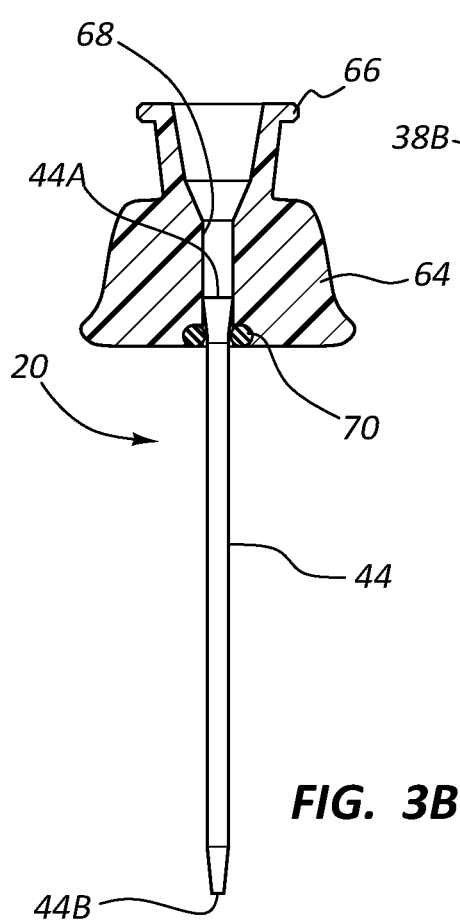
Figure 3C:
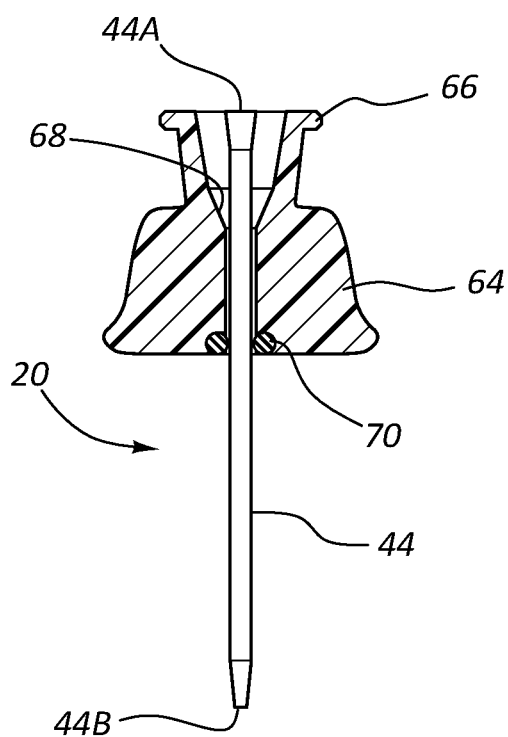

FIGS. 3A-3D depict various details of the catheter 20 according to one embodiment, wherein the hub 42 defines a base portion 64 and a connector portion 66 configured to enable the extension set 60 to operably connect with the catheter. The hub 42 includes a lumen 68 that cooperates with the cannula 44 to define a fluid path to allow the passage of fluids through the catheter. As shown, the cannula 44—which in this embodiment includes a sufficiently rigid material such as stainless steel, PEEK, or other suitable metals/thermoplastics/materials—is slidable with respect to the hub 42 so as to enable the total length of the catheter 20 to be adjusted—a relatively long length for a deep cannula distal tip placement as shown in FIG. 3B, and a relatively short length for a shallow cannula distal tip placement as shown in FIG. 3C. This in turn enables the hub 42 of the catheter 20 to rest against the skin surface 50, as shown in FIG. 2D, regardless of the depth of the distal tip 44B of the cannula 44. If not adjustable, the catheter may present a situation where the hub 42 is spaced apart from the skin surface 50, similar to what is shown in FIG. 2C.

Figure 3D:
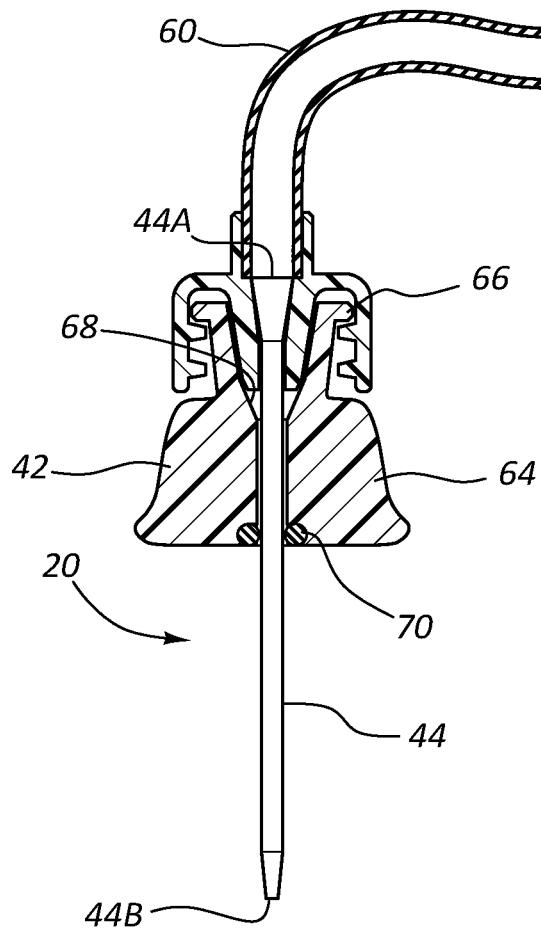

In greater detail, the variation in extension of the cannula 44 from the hub 42 is made possible by an O-ring 70 that is interposed within the lumen 68 between the base portion 64 of the hub 42 and an outer surface of the cannula 44, which in turn enables the cannula to longitudinally slide within the hub lumen in a fluid-tight arrangement. It is appreciated that the O-ring 70 can be located in other positions within the lumen 68 of the hub 42 and that other fluid sealing modes in addition to an O-ring can be utilized. FIG. 3D, shows that, in the present embodiment, the cannula 44 can be withdrawn into the hub 42 such that it extends past the connector portion 66 of the hub and into the extension set 60, thus enabling further shortening of the overall longitudinal length of the catheter 20.

Figure 4:
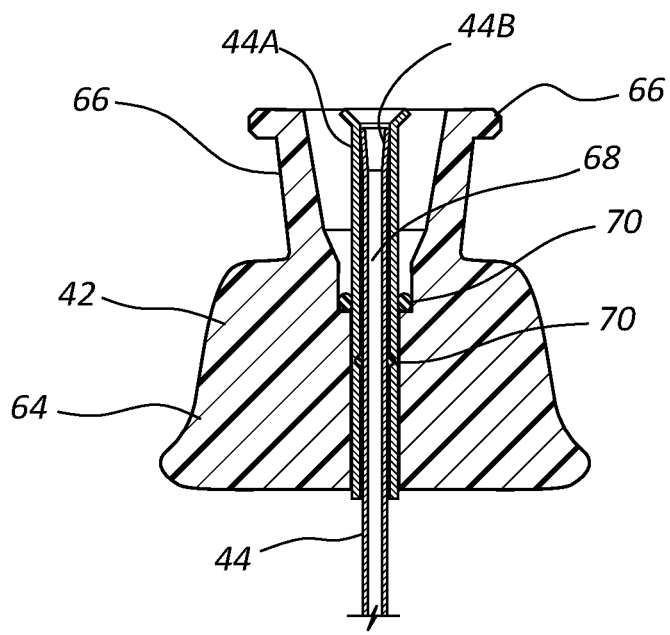
FIG. 4 is a cross-sectional side view of an intraosseous catheter according to one embodiment.

FIG. 4 depicts the catheter 20 according to another embodiment, wherein the cannula 44 includes a first cannula portion 44A and a second cannula portion 44B that are telescopically mated to one another with two O-rings 70 interposed therebetween and between the first cannula portion and the lumen 68 of the hub base portion 64 as to enable the cannula portions to extend and contract relative to one another and the hub base portion. Such a telescoping configuration can allow for greater variation in total longitudinal length of the catheter 20. Also, as shown, the proximal ends of the first and second cannula portions include radially extending lips that prevent separation of the cannula portions from each and from the hub when the cannula portions are fully extended. Though other gauge sizes are possible, in the present embodiment the first cannula portion 44A is a 15 gauge size while the second cannula portion 44B, which fits inside the first cannula portion, is an 18 gauge size. It is appreciated that one, two, or more telescoping portions can be employed.

Figure 5A:
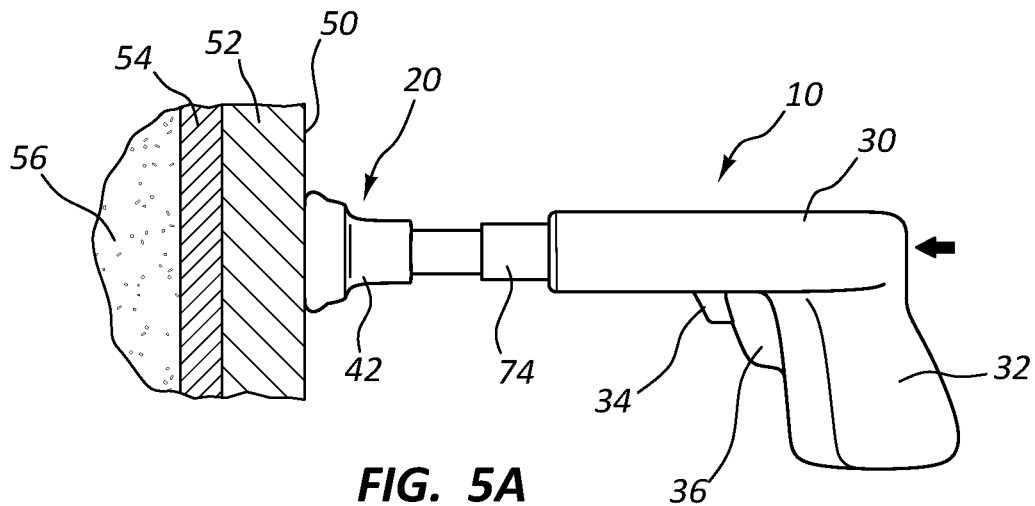
FIGS. 5A-5D depict various stages of use of an access device according to one embodiment.
Figure 5B:
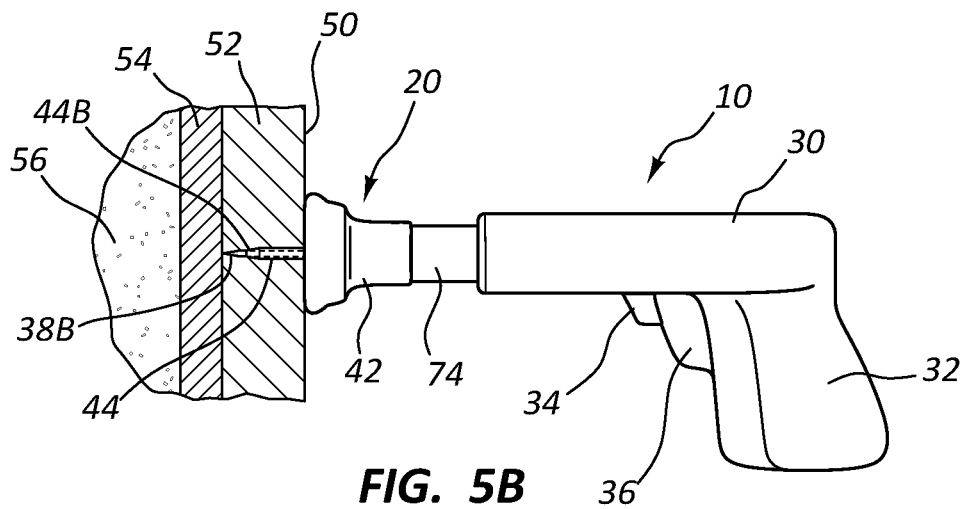

FIG. 5A depict various features and operation of the access device 10 according to one embodiment, wherein the body 30 includes a telescoping portion that initially shields the trocar 38 prior to access device use. During use of the access device 10, and as shown in FIG. 5A, the user grasps the body 30 of the access device and places the distal end 30B thereof against the skin surface 50. The distal tip 38B of the trocar 38 is then inserted via manual pushing through the skin surface 50 and subcutaneous tissue 52 of the patient until the distal tip of the trocar impacts a wall ("bone wall") 54 of the bone, as shown in FIG. 5B. Note that this action causes the telescoping portion 74 of the access device body 30 to collapse into the more proximal portion of the body so that the trocar 38 can extend from the body. Also, it is appreciated that this action causes the catheter cannula 44, which is disposed about the trocar 38, to be initially retracted at least partially within the catheter hub 42, then extend distally as the trocar extends distally toward the bone wall 54. The configurations of the catheter 20 shown in FIGS. 3A-3D and 4 are examples of suitable catheter configurations that can be utilized with the access device embodiment shown in FIGS. 5A-5D, though other catheter configurations are also possible. As has been discussed, the initial shielding of the trocar 38 by the telescoping portion 74 of the access device body 30 prevents inadvertent contact with the trocar by the user prior to trocar extension from the access device body. In one embodiment, the telescoping portion of the access device body only shields the trocar after use of the access device.

Figure 5C:
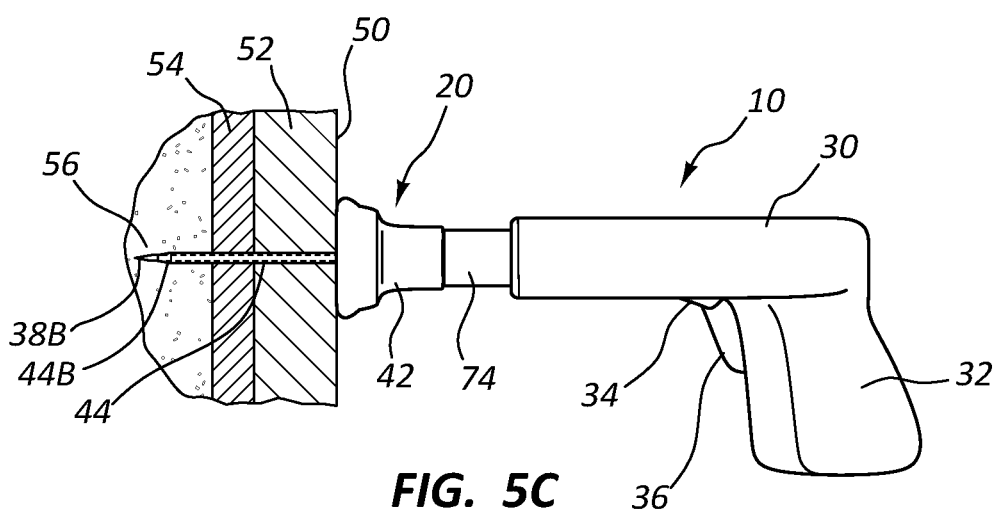

At this point, the safety switch 34 is disengaged by the user and the release trigger 36 is depressed by a finger of the user, which in turn causes the internal spring (or other suitable advancement mechanism) to distally drive the trocar distal tip 38B through the bone wall 54 and into the bone marrow 56 of the bone, as seen in FIG. 5C. This also places the distal tip 44B of the catheter cannula 44 in the bone marrow 56, as desired. Note that, due to the longitudinally extendable nature of the hub 42, the hub rests against the skin surface 50 at the commencement of and throughout the catheter insertion procedure, as seen in FIGS. 5A-5D.

As with the embodiment shown and discussed in connection with FIGS. 2A-2D, the access device 10 and the advancement mechanism are configured to advance the cannula distal tip 44B a predetermined distance into the bone. In this and other embodiments, it is appreciated that the predetermined distance can be varied according to user preference as discussed herein, and that the access device can be configured such that it is capable of advancing the catheter a distance into the bone that is not predetermined before use of the access device.

Figure 5D:
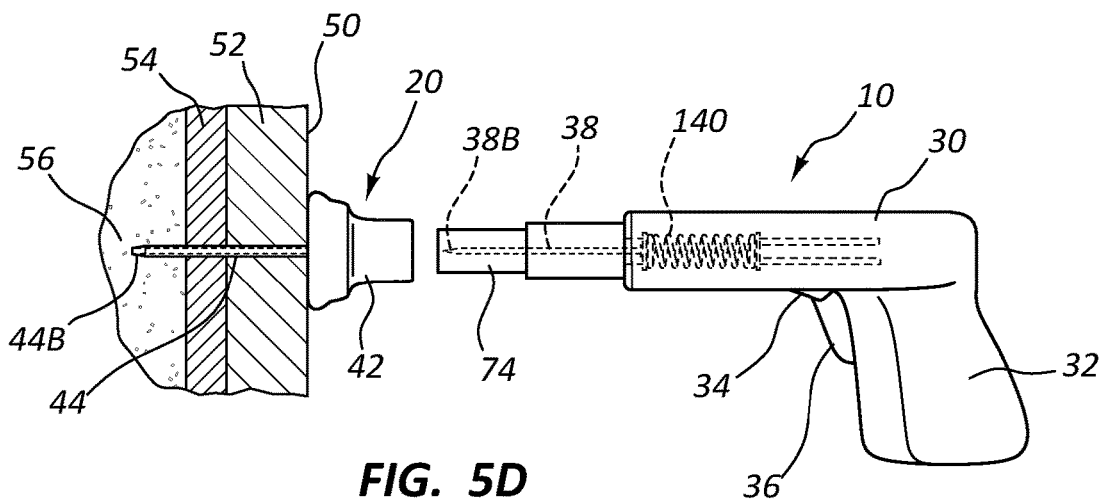

In FIG. 5D, the trocar 38 is withdrawn from the cannula 44 of the catheter 20 by proximally withdrawing the access device body 30, thus causing separation of the access device 10 from the catheter 20. As the access device body 30 is proximally withdrawn, the telescoping portion 74 distally extends to fully cover and shield the trocar 38 upon its removal from the catheter 20, thus preventing an inadvertent needle stick to the user. In one embodiment, interfering surfaces can be included on both the telescoping portion 74 and the catheter 20 to assist in the distal extension of the telescoping portion as seen in FIG. 5D. In another embodiment, the telescoping portion 74 can be manually extended by the user.

After withdrawal of the access device 10, the cannula 44 remains in place with its distal tip 44B disposed within the bone marrow 56, as shown. Note that the catheter hub 42 remains in place against the skin surface 50, as desired. The catheter 20 can be dressed, connected to the extension set 60, and otherwise made ready for infusion of fluids into the bone marrow 56 via the catheter cannula 44.

Figure 6:
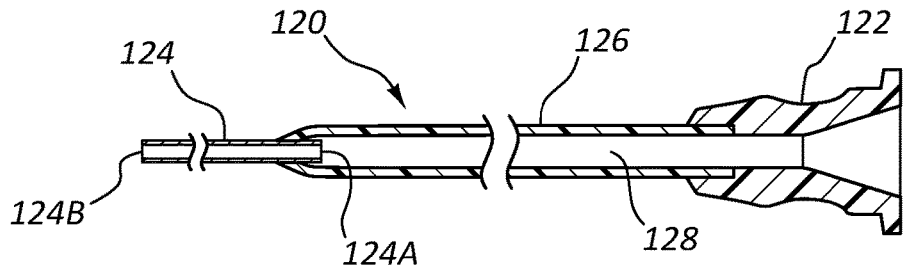
FIG. 6 is a cross-sectional side view of an intraosseous catheter according to one embodiment.
Figure 7:
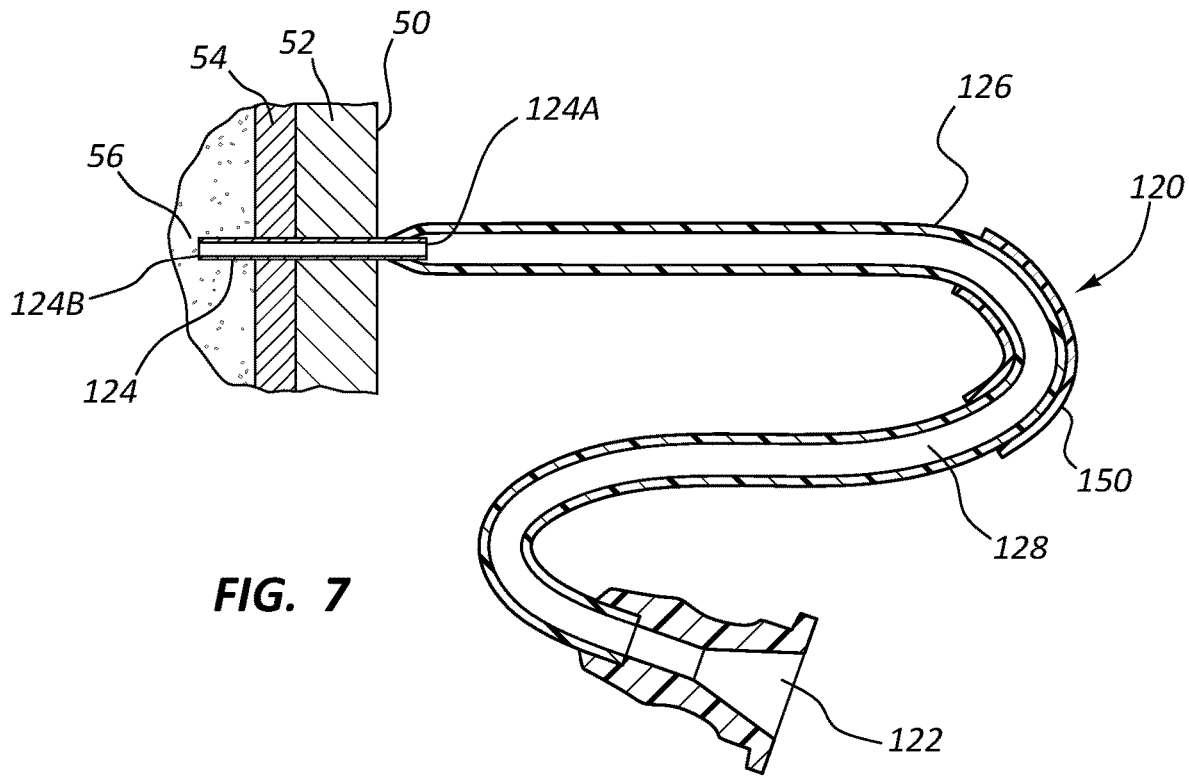
FIG. 7 is a cross sectional side view showing placement of the catheter of FIG. 6.
Figure 8:
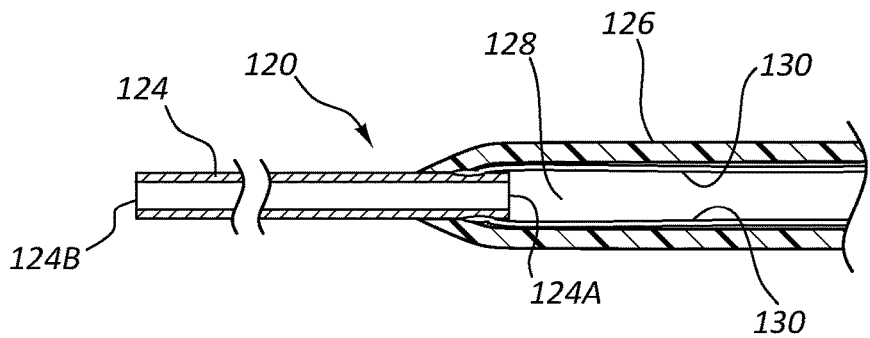
FIG. 8 is a cross-sectional side view of a portion of the catheter of FIG. 6.

FIGS. 6-8 depict details of an example of a catheter 120 that can be employed with the access device 10 according to one embodiment. As shown, the catheter 120 includes on a proximal end a hub 122 configured to operably connect with an extension set, and on a distal end a rigid cannula portion 124 extending between a proximal end 124A and a distal end 124B. A flexible catheter portion 126 operably connects between the hub 122 and the cannula portion 124 and overlaps the proximal end 124A of the cannula portion in the present embodiment. A lumen 128 that serves as a fluid pathway is defined by the hub 122, cannula portion 124, and the catheter portion 126. The cannula portion 124 includes a sufficiently rigid material to penetrate bone without buckling or collapsing, such as stainless steel, peek, or other suitable material including other metals and thermoplastics. The hub 122 and the catheter portion 126 include suitable thermoplastic or other materials in one embodiment.

FIG. 7 depicts the manner in which the catheter 120 is employed, wherein the cannula portion is shown inserted through the bone wall 54 such that its proximal end 124A resides external to the bone wall and its distal end 124B is disposed in the bone marrow 56. A distal segment of the catheter portion 126 extends between the bone wall 54 and the skin surface 50, while the remainder portion of the catheter resides outside the patient. In the present embodiment, a slidable elbow piece 150 is shown disposed over the catheter tube 126. During use, the elbow piece can be slid along the catheter tube 126 and positioned to help conform the catheter tube to the skin surface 50 at the point of exit from the patient body. The elbow piece can include a 90 degree other angle bend to assist with such conformation of the catheter tube 126.

Also note that, though FIG. 7 shows it extending out through the skin surface 50, the cannula portion 124 in one embodiment can be disposed completely internal to the patient body such that a distal portion of the catheter tube 126 is also disposed beneath the skin surface.

FIG. 8 shows that, in the present embodiment, securement wires 130 attached to the proximal end 124A of the cannula portion 124 extend proximally through the lumen 128 of the catheter portion 126 to the hub 122 where they are secured. The securement wires 130 provide necessary strength to enable the cannula portion 124 to be pulled from the bone wall 54 without separating from the rest of the catheter 120. Note that in one embodiment the securement wires 130 can be integrated into the wall of the catheter portion 126. In another embodiment, one, two, or more securement wires 130 can be included. In yet another embodiment, the securement wires 130 extend out past the proximal end of the hub 122. In another embodiment, the securement wires can take other forms, such as a securement ribbons, for instance. These and other variations are therefore contemplated.

Figure 9A:
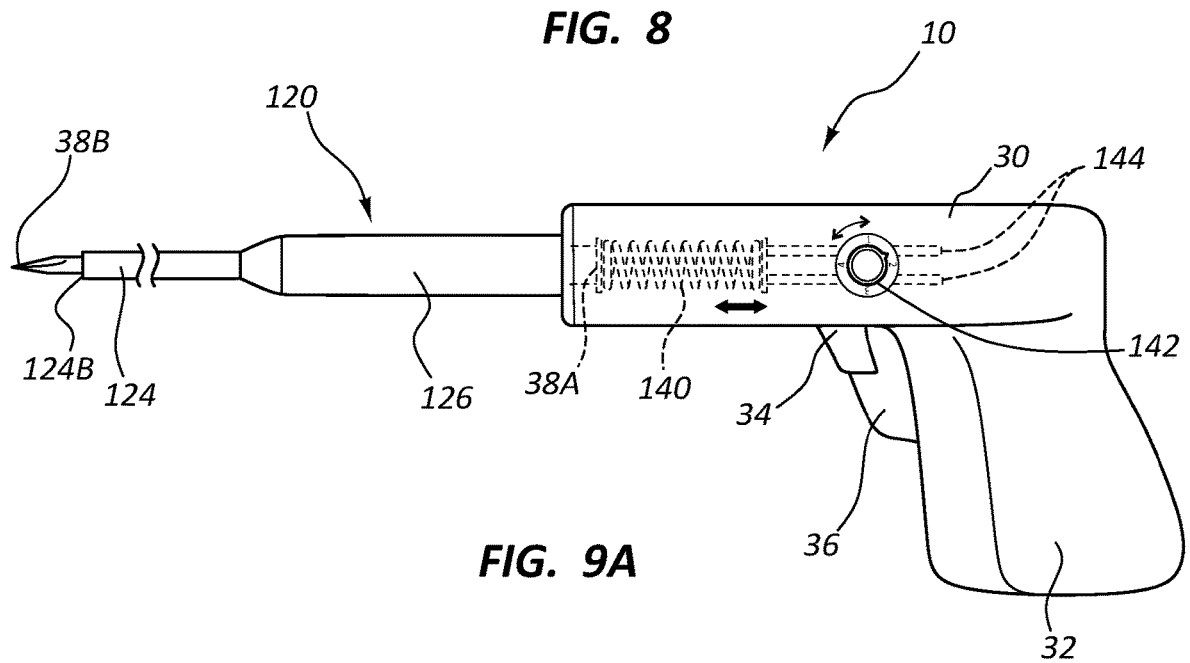
FIGS. 9A and 9B depict various views of the catheter of FIG. 6 and an access device used therewith.
Figure 9B:
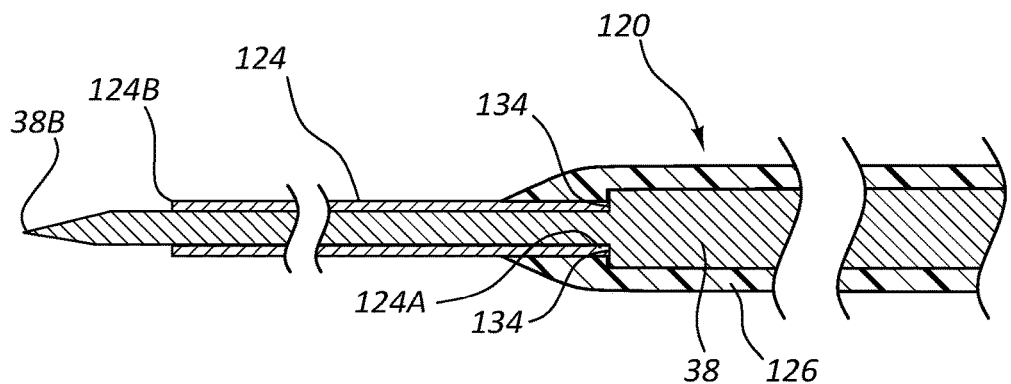

FIG. 9A shows that manner in which the catheter 120 is loaded on the trocar 38 of the access device 10. FIG. 9B shows that the trocar 38 in one embodiment can include a shoulder 134 against which the proximal end 124A abuts when the catheter 120 is disposed on the trocar. This provides the trocar 38 a surface against which to push to advance the catheter 124 through the bone wall 54 and into the bone marrow 56 during use of the access device 30 while still enabling the trocar to readily withdraw from the catheter after catheter placement is complete. Note that the particular location, size, and other configuration of the shoulder can vary from what is shown and described herein.

FIG. 9A further depicts details of an adjustment component configured to adjust the depth to which the advancement mechanism advances the distal tip 38B of the trocar 38 and the catheter 120 (Note that the present discussion regarding the adjustment component can be applied to other embodiments herein). As shown, a spring 140 is included within the access device body 30 and configured as an advancement mechanism to provide a distal advancement force as with other embodiments herein) to the trocar 38 via its proximal end 38A. An adjustment component, here embodied as a rotary adjustment dial 142, is disposed on the surface of the access device body 30 and is movable by a user of the access device to select a predetermined depth to which the distal tip 38B of the trocar 38, and correspondingly, the distal tip 124B of the catheter 120, will be advanced by the spring 140. In the present embodiment, the adjustment dial 142 is operably connected to one or more control arms 144 that are configured to vary the pre-actuation length of the spring 140. This in turn lessens or increases the potential energy stored in the spring 140 prior to actuation, thus providing for relatively more shallow or deep advancement of the trocar 38 and catheter 120 into the bone. In addition to this, other adjustment components and advancement mechanisms can be employed, in other embodiment.

In light of the above, it is appreciated that the spring 140 serves as one example of a selective means for advancing the trocar and the catheter. Note that the spring 140 is considered selective as it is actuated selectively by the user via a trigger or other suitable component. It is appreciated that other structures and components can be employed to provide the same functionality, in other embodiments.

Figure 10:
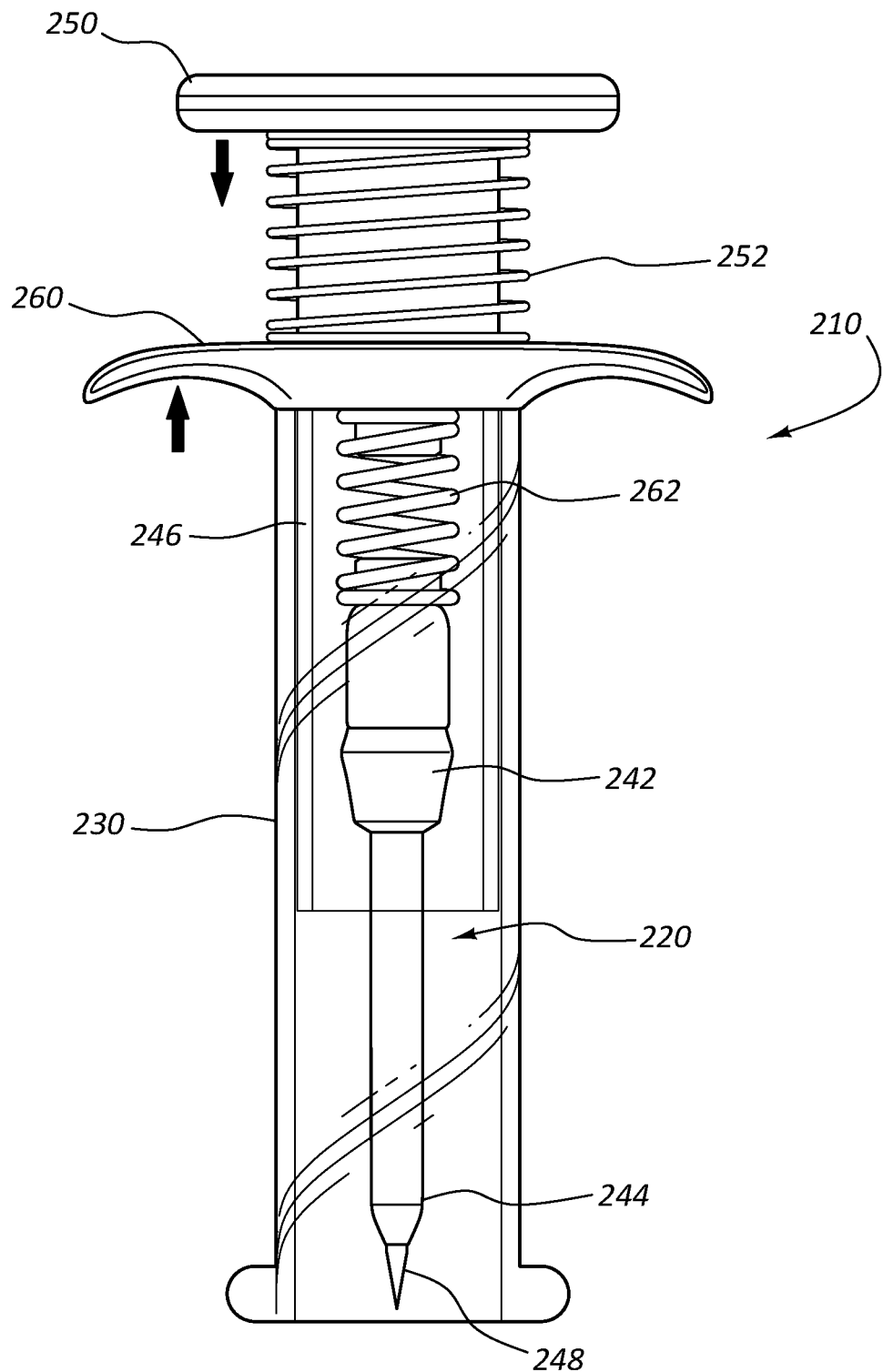
FIG. 10 is a cross-sectional side view of an intraosseous access device according to one embodiment.

FIG. 10 depicts details of an intraosseous access device ("access device") 210 according to one embodiment, including an elongate body 230 inside of which is disposed an intraosseous catheter ("catheter") 220, also referred to as an intraosseous cannula. As before, the catheter 220 includes a hub 242 from which distally extends a cannula 244. The catheter 220 in the present embodiment is slidably disposed over a trocar needle ("trocar") 248 and received within a cartridge 246 that itself is disposed within the access device body 230, as shown.

The access device 210 further includes an advancement mechanism configured to selectively advance the trocar 248 and catheter 220 included therewith in a distal direction during use of the access device 210. In the present embodiment, the advancement mechanism includes a first actuator, here implemented as a first trigger 250 configured to selectively activate a first spring 252, and a second actuator, here implemented as a second trigger 260 configured to selectively actuate a second spring 262. The first spring 252 is a relatively low-force spring configured to provide, when actuated by the first trigger 250 (e.g., by manually depressing the first trigger in a distal direction), a force to distally advance the catheter-containing cartridge 246 out a distal end of the access device body 230 a predetermined distance. This action is employed during use of the access device 210 to advance the trocar 248 and catheter 220 through the skin surface and tissue of the patient to the bone wall. Note that in the present embodiment, the distal end of the cartridge 246 rests against the skin surface after actuation of the first trigger 250 to distal advance the catheter 220.

In contrast, the second spring 262 is a relatively high-force spring configured to provide, when actuated by the second trigger 260 (e.g., by manually pulling the second trigger in a proximal direction), a force to distally advance the catheter 220 from the open distal end of the cartridge 246 a further predetermined distance. This action is employed during use of the access device 210 to advance the distal ends of the trocar 248 and the catheter 220 through the bone wall and into the bone marrow of the patient. The use of the relatively high-force spring 262 is necessary to enable the trocar 248 and catheter 220 to penetrate the relatively stiff and rigid bone wall. Once the distal end of the catheter 220 is in place in the bone marrow of the patient, the trocar can be withdrawn from the patient body by proximally withdrawing the access device body 230 by the user.

It is appreciated that the second spring 262 serves as an example of selective means for advancing the trocar 248 and the catheter 220, and is thus configured to apply the necessary amount of force to cause the above-described penetration of the patient bone wall. The second spring 262 is considered selective as it is actuated by a user via a trigger or other suitable component. It is appreciated that other structures and components can be employed to provide the same functionality, in other embodiments. Note that the first and second springs 252, 262 can be configured to cause penetration of the trocar 248/catheter 220 to different predetermined distances into the bone. In one embodiment, the access device is configured such that the first and second springs cause penetration to a single predetermined depth for each spring. In another embodiment, the access device includes the ability to adjust the force of one or more of the springs to vary the amount of trocar/catheter penetration. These and other modifications are therefore contemplated.

Figure 11:
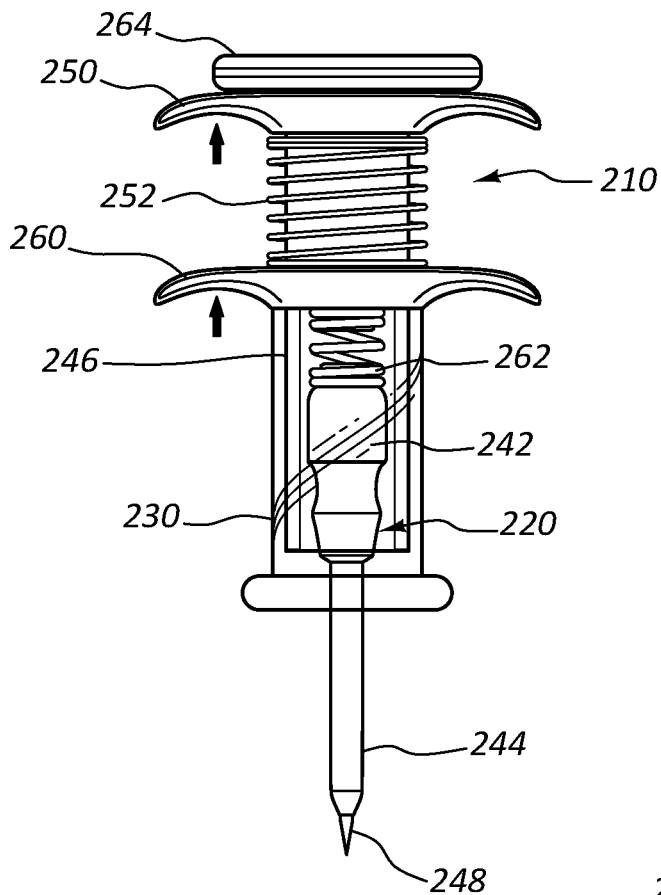
FIG. 11 is a cross sectional side view of an intraosseous access device according to one embodiment.

FIG. 11 depicts the access device 210 according to another embodiment, wherein both the first trigger 250 and the second trigger 260 are configured as triggers to be manually pulled in the proximal direction to actuate the first spring 252 and the second spring 262, respectively. Note that FIG. 11 shows the configuration of the access device 210 after actuation of the first spring 252 by manual proximal pulling of the first trigger 250, wherein the catheter 220 is partially extended from an open distal end of the access device body 230, but before actuation of the second spring 262 by manual proximal pulling of the second trigger 260, which causes further distal ejection of the catheter. In one embodiment, it is appreciated that the access device can be configured such that actuation of the first spring, second spring, or both springs can be performed automatically. Also, in one embodiment, the relatively strong second spring can be sized to fit within (such as concentrically, for instance) the relatively weaker first spring. In another embodiment, the first spring is sized to be received within the second spring.

Figure 12:
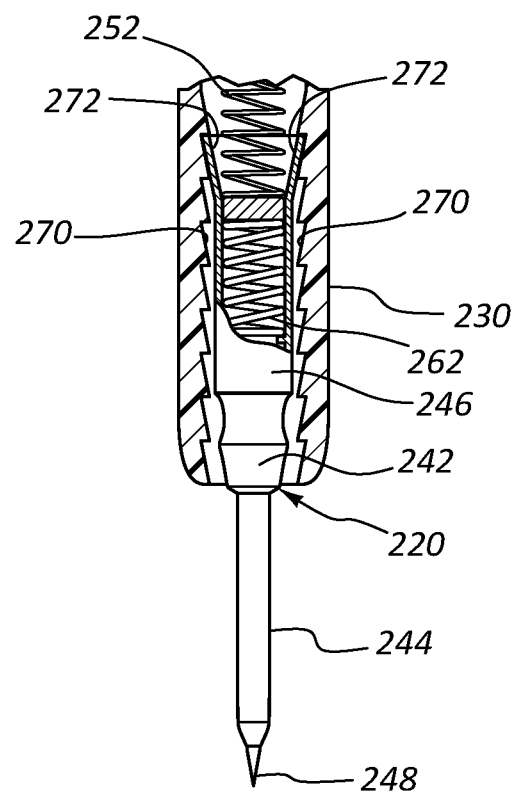
FIG. 12 is a cross-sectional side view of a intraosseous access device according to one embodiment.

FIG. 12 depicts details of an advancement mechanism according to another embodiment, wherein the access device body 230 defines on an inner surface thereof a plurality of ratchet teeth 270 that are configured to engage with two radially extending engagement arms 272 that are included on a proximal portion of the cartridge 246 holding the catheter 220. This arrangement enables the cartridge 246 and included catheter 220 to distally advance in a step-wise fashion without having the ability to withdraw back into the access device body 230. Note that the ratchet components can vary in shape, size, position, and other configuration from what is shown and described herein.

Figure 13:
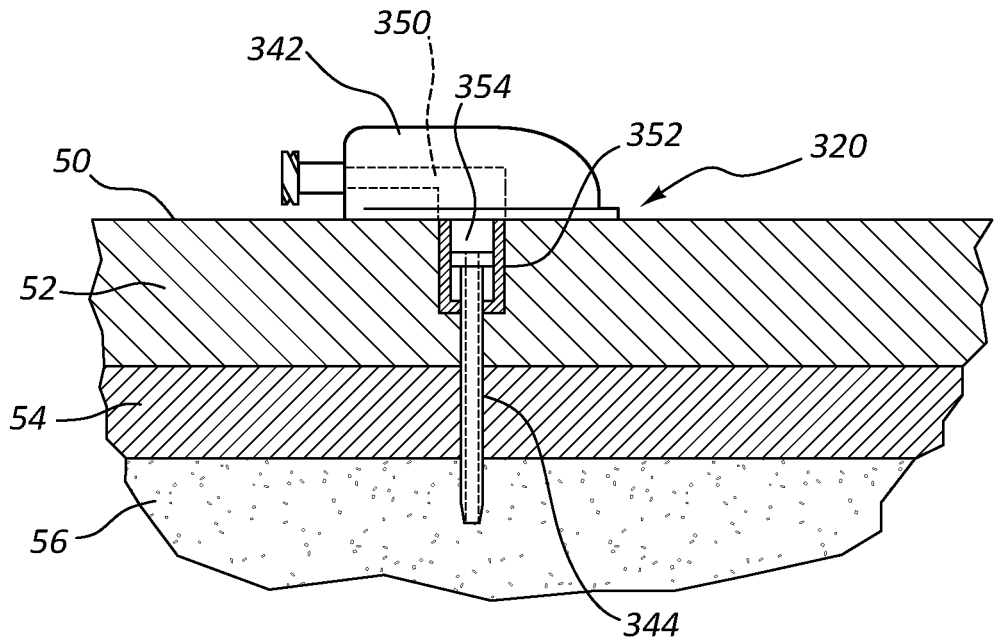
FIG. 13 is a cross-sectional side view of an intraosseous catheter according to one embodiment.
Figure 14:
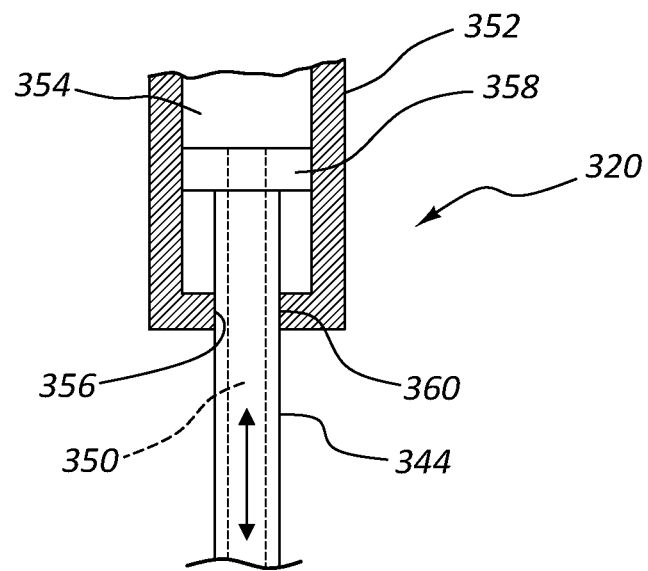
FIG. 14 is a cross-sectional side view of a portion of the catheter of FIG. 13.

FIGS. 13 and 14 depict details of an intraosseous catheter 320 according to one embodiment, including a hub 342 and an elongate cannula 344 distally extending therefrom. The catheter 320 is shown in FIG. 13 in place within a patient, with a distal tip of the cannula 344 extending to the bone marrow 56. A lumen 350 is defined by the catheter 320 to enable infusion of medicaments or other fluids to the bone marrow 56.

FIG. 14 shows that the catheter 320 is adjustable in total length. In light of this, in the present embodiment the hub 342 includes a slide tube defining a cavity 354 and an opening 356 to the cavity. Correspondingly, the cannula 344 is received through the opening 356 and includes on its proximal end a radially extending rim 358 configured to slide proximally/distally within the cavity 354, thus enabling the total longitudinal length to vary according to the position of the rim within the cavity. A seal 360 is placed about the opening 356 to ensure a fluid tight seal between the cannula and the opening. In this way, the catheter 320 can vary in desired length according to bone depth and user preference. If desired, the hub 342 can be adhered to the skin surface 50 after adjustment of the catheter 320 is made to enable the hub to rest against the skin surface.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An intraosseous access device, comprising:
    a device body;
    a trocar needle coupled to the device body;
    an intraosseous catheter removably disposed on the trocar needle;
    a first advancement member configured to provide a first distal advancement force sufficient to distally advance a distal tip of the trocar needle and the intraosseous catheter through a skin surface to an external surface of a bone of a patient; and
    a second advancement member configured to provide a second distal advancement force sufficient to distally advance the distal tip of the trocar needle and the intraosseous catheter through the external surface of the bone after the first advancement member has advanced the distal tip of the trocar needle and the intraosseous catheter to the external surface of the bone.

2. The intraosseous access device according to claim 1, wherein the first advancement member is a first spring and wherein the second advancement member is a second spring, the second distal advancement force provided by the second spring being greater in magnitude relative to the first distal advancement force provided by the first spring.

3. The intraosseous access device according to claim 2, wherein the first spring is actuated by a first trigger and wherein the second spring is actuated by a second trigger.

4. The intraosseous access device according to claim 3, wherein at least one of the first trigger and the second trigger is actuated via a proximally directed manual force provided by a user.

5. The intraosseous access device according to claim 3, wherein at least one of the first trigger and the second trigger is actuated automatically.

6. The intraosseous access device according to claim 2, wherein the second spring has a portion positioned concentrically within the first spring.

7. The intraosseous access device according to claim 1, wherein the trocar needle extends distally from the device body prior to use.

8. The intraosseous access device according to claim 1, wherein the second advancement member is configured to distally advance the trocar needle and the intraosseous catheter a predetermined depth into an internal portion of the bone.

9. The intraosseous access device according to claim 8, wherein the predetermined depth is adjustable via an adjustment component.

10. The intraosseous access device according to claim 1, wherein the intraosseous access device further includes a safety switch.

11. The intraosseous access device according to claim 1, wherein the second advancement member is configured to distally advance a distal tip of the intraosseous catheter into an intraosseous portion of the bone.

12. The intraosseous access device according to claim 11, wherein the bone is selected from the group consisting of a tibia, a sternum, and a humerus.

13. The intraosseous access device according to claim 1, wherein the device body includes a plurality of ratchet teeth on an inner surface.

14. The intraosseous access device according to claim 13, wherein the intraosseous catheter has a proximal end coupled to a cartridge, the cartridge comprising a proximal end designed to engage the plurality of ratchet teeth.

* * * * *